US008211476B2

(12) United States Patent
Kanamaru et al.

(10) Patent No.: US 8,211,476 B2
(45) Date of Patent: Jul. 3, 2012

(54) COMPOSITIONS AGAINST ROTAVIRUS INFECTION AND PROCESSES FOR PRODUCING THE SAME

(75) Inventors: Yoshihiro Kanamaru, Gifu (JP); Yoshitaka Nakamura, Kanagawa (JP); Takeshi Takahashi, Kanagawa (JP); Shinya Nagafuchi, Kanagawa (JP); Makoto Yamaguchi, Kanagawa (JP); Hideo Ohtomo, Kanagawa (JP); Kenichi Nakazawa, Saitama (JP)

(73) Assignee: Meiji Co., Ltd., Tokyo (JP)

( * ) Notice: Subject to any disclaimer, the term of this patent is extended or adjusted under 35 U.S.C. 154(b) by 1478 days.

(21) Appl. No.: 10/548,906

(22) PCT Filed: Mar. 11, 2004

(86) PCT No.: PCT/JP2004/003185
§ 371 (c)(1),
(2), (4) Date: Jun. 22, 2006

(87) PCT Pub. No.: WO2004/080475
PCT Pub. Date: Sep. 23, 2004

(65) Prior Publication Data
US 2006/0240115 A1   Oct. 26, 2006

(30) Foreign Application Priority Data
Mar. 14, 2003   (JP) ................... 2003-070669

(51) Int. Cl.
*A61K 35/20* (2006.01)
(52) U.S. Cl. ........................................ 424/535
(58) Field of Classification Search .......... None
See application file for complete search history.

(56) References Cited

U.S. PATENT DOCUMENTS

| 5,066,491 | A | * | 11/1991 | Stott et al. ................ 424/157.1 |
| 5,503,864 | A | | 4/1996 | Uchida et al. |
| 5,667,797 | A | | 9/1997 | Peterson et al. |
| 5,747,031 | A | | 5/1998 | Ruch et al. |
| 5,747,647 | A | | 5/1998 | Stack et al. |
| 5,834,042 | A | * | 11/1998 | Savolainen .................... 426/41 |

FOREIGN PATENT DOCUMENTS

| AU | 666512 | 2/1996 |
| EP | 0 391 416 A1 | 10/1990 |
| EP | 0391416 | 10/1990 |
| EP | 0605219 | 7/1994 |
| EP | 1046344 | 10/2000 |
| EP | 1046344 B1 | 10/2000 |
| JP | 63-133941 | 6/1988 |
| JP | 63-135336 | 6/1988 |
| JP | 3-072432 | 3/1991 |
| JP | 3-218318 | 9/1991 |
| JP | 5-236883 | 9/1993 |
| JP | 5-244875 | 9/1993 |
| JP | 5-269353 | 10/1993 |
| JP | 6-189679 | 7/1994 |
| JP | 8-099896 | 4/1996 |
| JP | 8-116875 | 5/1996 |
| JP | 9-509320 | 9/1997 |
| JP | 10-501698 | 2/1998 |
| JP | 10-505828 A | 6/1998 |
| JP | 11-512746 | 11/1999 |
| JP | 2000-300183 | 10/2000 |
| JP | 2002-255824 | 9/2002 |
| NZ | 542981 | 9/2008 |
| WO | WO 94/09651 | 5/1994 |
| WO | WO 96/08269 A1 | 3/1996 |
| WO | WO 9712901 | 4/1997 |
| WO | WO 2004/080475 | 9/2004 |

OTHER PUBLICATIONS

Kumar et al. Journal of Dairy Science, vol. 55, Issue 9, Sep. 1972, pp. 1237-1242.*
Filtration Spectrum, 2011, retrieved from URL: <http:/www.geafiltration.com/technology/cross_flow_filtration> on Feb. 25, 2011.*
Dejmek, P. et al. "Food applications of membrane technology in Europe" *Proceedings of the 5th Spring Meeting of the Membrane Research Council on Food*, May 22, 1993, pp. 36-45.
De Koning, P. J. et al. "Effects of some proteinase inhibitors and of the Maillard reaction on the processes of age-thinning and gelation of UHTST-sterilized concentrated casein micelle dispersions" *Neth. Milk Dairy J.*, 1985, pp. 37-47, vol. 39.
De Wit, J. N. et al. "Ultrafiltration of cheese whey and some functional properties of the resulting whey protein concentrate" *Neth. Milk Dairy J.*, 1975, pp. 198-211, vol. 29.
Duffy, L.C. et al. "Effectiveness of *Bifidobacterium bifidum* in mediating the clinical course of murine rotavirus diarrhea" *Pediatric Research*, Jun. 1994, pp. 690-695, vol. 35, No. 6.
Ishida, S. et al. "Rotavirus Vaccines" *The Journal of Pediatric Practice*, 2000, pp. 1045-1049, vol. 63, No. 7. (English translation provided).
Kiyosawa, I. "Progress in recent researches on the whey protein concentrates and their functional properties" *Milk Science*, 2002, pp. 13-26, vol. 51, No. 1. (English summary provided).
Kvistgaard, A. S., et al. "Inhibitory effects of human and bovine milk constituents on rotavirus infections" *J. Dairy Sci.*, Dec. 2004, pp. 4088-4096, vol. 87, No. 12.
Matsumoto, M. et al. "Anti bovine rotavirus polypeptide from buttermilk" *Nihon Chikusan Gakkaiho*, 2002, pp. 49-56, vol. 73, No. 1. (English abstract provided).
Maubois, J. L. "Current uses and future perspectives of MF technology in the dairy industry" *Bulletin of the IDF*, 1997, pp. 37-40, vol. 320.
Morr, C. V. et al. "Whey protein concentrates and isolates: processing and functional properties" *Critical Reviews in Food Science and Nutrition*, 1993, pp. 431-476, vol. 33, No. 6.
Nielson, A. et al. "Powdered whey protein concentrate" *Danish Dairy and Food Industry . . . Worldwide*, 1996, pp. 72-73, vol. 10.

(Continued)

Primary Examiner — Allison Ford
Assistant Examiner — Yvonne Pyla
(74) Attorney, Agent, or Firm — Saliwanchik, Lloyd & Eisenschenk

(57) ABSTRACT

The present inventors discovered that microfiltration retentates of whey, and products obtained by treating whey using centrifugation and/or ammonium sulfate precipitation, have the activity of inhibiting rotavirus infection.

5 Claims, 1 Drawing Sheet

OTHER PUBLICATIONS

Olesen, N. et al. "Microfiltration. The influence of operation parameters on the process" *Milchwissenschaft*, 1989, pp. 476-479, vol. 44, No. 8.

Patel, M. T. et al. "Studies on whey protein concentrates. 2. Foaming and emulsifying properties and their relationships with physicochemical properties" *J. Dairy Sci.*, 1990, pp. 2731-2740, vol. 73, No. 10.

Sugahara, T. et al. "Immunostimulation effects of proteose-peptone component 3 fragment on human hybridomas and peripheral blood lymphocytes" *Biochimica et Biophysica Acta*, Sep. 15, 2005, pp. 233-240, vol. 1725, No. 2.

Wolber, F. M. et al. "Supplemental dietary whey protein concentrate reduces rotavirus-induced disease symptoms in suckling mice" *J. Nutr.*, Jun. 2005, pp. 1470-1474, vol. 135, No. 6.

Yolken, R. H. et al. "Human milk mucin inhibits rotavirus replication and prevents experimental gastroenteritis" *J. Clin. Invest.*, Nov. 1992, pp. 1984-1991, 1992, vol. 90, No. 5.

Kanamaru et al. "Bovine milk fraction containing high-molecular-weight glycoprotein that strongly inhibits replication of human rotavirus" *Journal of the Agricultural Chemical Society of Japan*, 2002, pp. 400-401, vol. 76, No. 4.

Kanamaru et al. "Bovine milk protein that strongly inhibits human rotavirus infection" *Annual Meeting of Japan Society for Bioscience, Biotechnology and Agrochemistry*, Mar. 5, 2003, p. 28 (#1M2p10).

Nagai et al. "Bovine milk protein resembling a component for human rotavirus cell receptor" *Annual Meeting of Japan Society for Bioscience, Biotechnology Agrochemistry*, Mar. 5, 2003, p. 218, (#3A19a05).

Anonymous "Protein concentration and sample clarification" [online] XP002583956 Millipore Retrieved from the Internet: URL: http://www.millipore.com/immunodetection/id3/concentration, [retrieved on May 25, 2010] Figure: Comparison of ultrafiltration with other commonly used membrane separation techniques.

Kanamaru et al. "A high-Mr glycoprotein fraction from cow's milk potent in inhibiting replication of human rotavirus in vitro" *Biosci. Biotechnol. Biochem.*, 1999, pp. 246-249, vol. 63, No. 1.

Got, R. "Fractionnement des protéines du lactosérum humain" *Clinica Chimica Acta*, 1965, pp. 432-441, vol. 11, with English abstract.

Song et al. "Antivirus activities in the colostrums of cows that prevent diarrhea caused by human rotavirus" *Mitchwissenschaft*, 1999, pp. 430-433, vol. 54, No. 8.

Superti et al. "Antirotaviral activity of milk proteins: lactoferrin prevents rotavirus infection in the enterocyte-like cell line HT-29" *Med Microbiol Immunol.*, Oct. 1997, pp. 83-91, vol. 186, Nos. 2-3.

Dominguez et al., "Effect of Heat Treatment on the Antigen-Binding Activity of Anti-Peroxidase Immunoglobulins in Bovine Colostrum," *J Dairy Sci*, Dec. 1997, vol. 80, No. 12, pp. 3182-3187.

Pearce, "Thermal Denaturation of Whey Protein," *Bulletin of the IDF*: 238, Chapter 3, pp. 17-23.

Fox et al., "Milk Proteins", *Dairy Chemistry and Biochemistry*, 1998, 1ed., pp. 146, 147, 195, Blackie Academic & Professional, London, United Kingdom.

Codex Alimentarius Comission, "Milk and Milk Products", *Codex Alimentarius*, 2011, 2ed., pp. 1-244, Rome, Italy.

Otani et al., Production and utilization of bovine milk immunoglobulins specific to pathogenic microorganisms, *Milk Science*, 1998, vol. 47, No. 2, pp. 63-75.

* cited by examiner

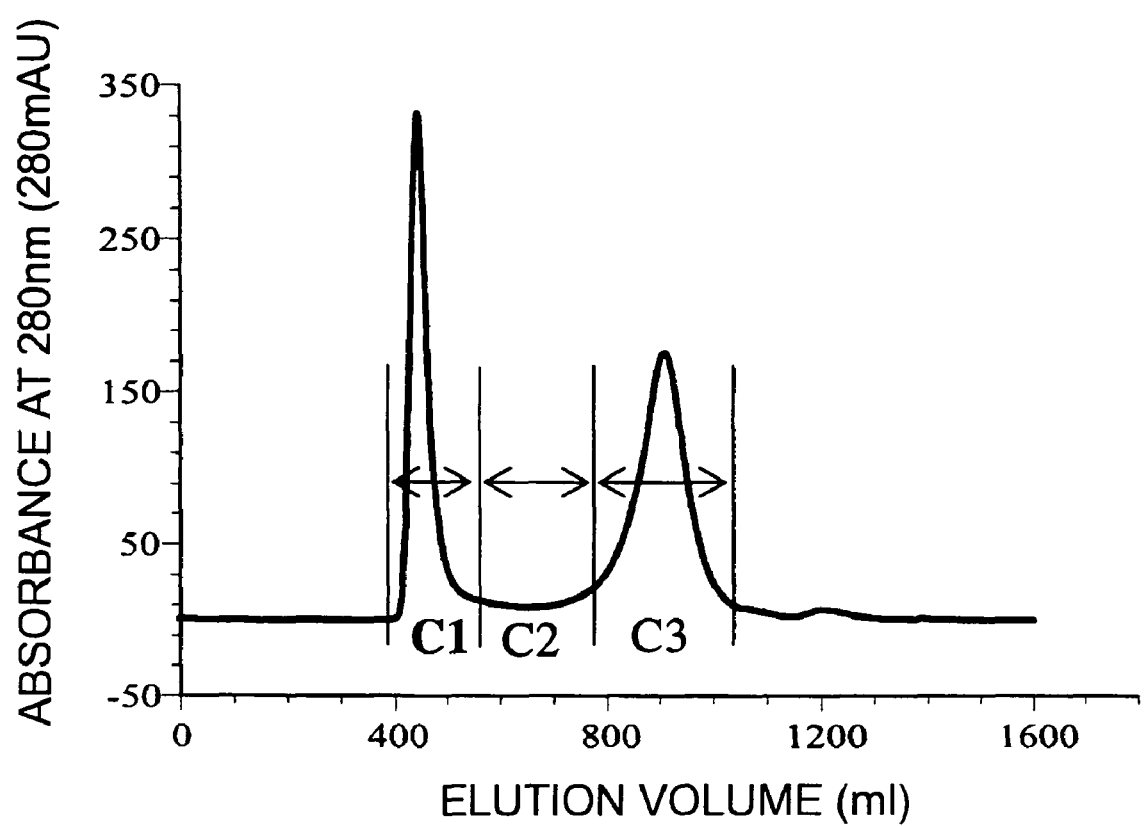

COMPOSITIONS AGAINST ROTAVIRUS INFECTION AND PROCESSES FOR PRODUCING THE SAME

This application is a National Stage Application of International Application Number PCT/JP2004/003185, filed Mar. 11, 2004; which claims priority to Japanese Application 2003-070669, filed Mar. 14, 2003.

TECHNICAL FIELD

The present invention relates to compositions against rotavirus infection, processes for producing the same, and food compositions against rotavirus infection that comprise effective doses of the compositions against rotavirus infection.

BACKGROUND ART

The infantile winter diarrhea caused by human rotavirus is a severe diarrheic disease leading to pyrexia, vomiting, diarrhea, and dehydration, mainly in infants aged two or under. In Japan, infantile winter diarrhea is sometimes referred to as white diarrhea due to the light gray appearance of stools; however, it is clearly a human rotavirus infection. In the U.S., 3,500,000 children aged five or under suffering from diarrhea are annually diagnosed with a rotavirus infection; of these 55,000 are hospitalized, and 20 die. Worldwide, about 600,000 infants die annually from this disease, mainly in developing countries. Epidemiological surveys conducted in developed countries suggest that merely improving sanitary conditions cannot reduce the prevalence of rotavirus infection. The worldwide development of rotavirus vaccines has therefore been promoted as a countermeasure against such infections.

In both developed and developing countries, rhesus rotavirus tetravalent (RRV-TV) vaccine was found to be highly effective in preventing the severe diarrhea caused by rotavirus. In August 1998, the U.S. Food and Drug Administration approved RRV-TV vaccine as the first rotavirus vaccine in the world. However, the U.S. Centers for Disease Control and Prevention have since reported intussusception as a side effect of RRV-TV vaccine, and its administration has been discontinued (see Non-Patent Document 1, for example).

On the other hand, food constituents or food compositions that prevent rotavirus infection have been proposed, including immunoglobulins in colostrum and compositions thereof (see Patent Document 1, for example), bovine ic-casein (see Patent Document 2, for example), milk mucin (see Non-Patent Document 2, for example), buttermilk-derived polypeptides (see Non-Patent Document 3, for example), and such. However, these substances have yet to be assessed. Thus, the arrival of novel compositions against rotavirus infection that are effective in inhibiting rotavirus infections, and of food compositions that comprise the aforementioned compositions, is still anticipated.

[Non-Patent Document 1] Ishida Shinichi et al., "Rotavirus vaccine" The Journal of Pediatric Practice (Shonika Sinryo) Vol. 63, 2000, p. 1045-1049

[Non-Patent Document 2] Yolken, R. Y et al., "Human Milk Mucin Inhibits Rotavirus Replication and Prevents Experimental Gastroenteritis" J. Clin. Invest., Vol. 90, 1992, p. 1984-1991

[Non-Patent Document 3] Matsumoto Mitsuharu et al., "Buttermilk-derived anti-bovine rotavirus polypeptide" Nihon Chikusan Gakkaiho, Vol. 73, 2002, p. 49-56

[Patent Document 1] Japanese Patent Application Kokai Publication No. (JP-A) H3-72432 (unexamined, published Japanese patent application)

[Patent Document 2] Japanese Patent Kohyo Publication No. (JP-A) H10-505828 (unexamined Japanese national phase publication corresponding to a non-Japanese international publication)

DISCLOSURE OF THE INVENTION

An objective of the present invention is to provide novel food compositions that are effective at preventing rotavirus infections. Another objective of this invention is to provide foods that comprise an effective dose of these compositions. A further objective of this invention is to provide livestock feeds that comprise an effective dose of these compositions.

As a result of studies to achieve the above-described objectives, the present inventors discovered that retentates obtained by treating whey by microfiltration (MF), fractions obtained by centrifuging whey, and/or fractions obtained by subjecting whey to ammonium sulfate precipitation (also referred to as an ammonium sulfate fractionation method, ammonium sulfate salting-out method, or ammonium sulfate precipitation method) have a strong activity of inhibiting rotavirus infection. They further discovered that the activity of inhibiting rotavirus infection was not lost, even after heat-treating of these retentates or fractions. More specifically, the present invention comprises:

(1) a composition having an activity of preventing rotavirus infection, wherein said composition is a microfiltration retentate of whey, a solution obtained by treating whey by centrifugation and/or ammonium sulfate precipitation, or a dehydrated product thereof;

(2) the composition of (1), wherein the micropore diameter of the microfiltration membrane ranges from 0.004 to 1.4 μm;

(3) the composition of (1), wherein the centrifugal force ranges from 300 to 30 000 g;

(4) the composition of (1), wherein the saturation level of ammonium sulfate precipitation ranges from 30 to 100%;

(5) a food having an activity of preventing rotavirus infection and comprising an effective dose of the composition of any one of (1) to (4);

(6) the food of (5), where the food is selected from the group consisting of infant formula, a food product for the elderly, a food with health claims, and a food product for the ill;

(7) a livestock feed having an activity of preventing rotavirus infection, and comprising an effective dose of the composition of any one of (1) to (4);

(8) a use of the composition of any one of (1) to (4) for manufacturing the food of (5) or (6); and, (9) a use of the composition of any one of (1) to (4) for manufacturing the livestock feed of (7).

Whey is classified into two groups: sweet whey and acid whey. Sweet whey is a by-product of aged type cheeses, and has a pH of 5.9 to 6.3, tasting sweet. On the other hand, acid whey is obtained during the manufacture of non-aged, fresh type cheeses, and usually has a pH of 4.4 to 4.6, tasting sour. Whey obtained during the manufacture of casein is also acid whey. The general compositions of sweet whey and acid whey are shown in Table 1 (Milk Science Vol. 51, No. 1, 2002). The present invention comprises both sweet whey and acid whey.

The whey used in this invention is prepared by standard methods, using as a starting material the milk of lactating cows, or the concentrated or dehydrated products thereof (hereinafter these may be collectively referred to as milk). Further, in the present invention, milk from mammals in addition to humans and cows can also be used. In general, after clarification, raw milk is pasteurized by methods such as High Temperature Short Time (HTST) (heating at 72° C. to 75° C. for 15 seconds), Ultra High Temperature (UHT) (heating at 120° C. to 150° C. for 1 to 3 seconds), etc. Thereafter, whey can be produced by two methods: One is a method for producing sweet whey. In this method, various rennets (derived from animals, microorganisms and plants) are added to pasteurized milk or to skim milk. Skim milk is obtained by warming pasteurized milk to about 30 to 60° C., centrifuging at a force of several hundred or more G, and de-fatting by removing the fat as cream. That is, this is a method for separating whey as a solution when manufacturing hard, semi-hard, or soft cheeses, and rennet caseins. The second method is for producing acid whey. In this method, acids (organic acids such as acetic acid and lactic acid, or inorganic acids such as hydrochloric acid and sulfuric acid) are added to skim milk obtained by a method similar to those described above. Specifically, acid whey is obtained by using acid to adjust the pH of skim milk to 4.6, and then using filtration, centrifugation, and the like to remove the isoelectrically precipitated casein. In addition to these methods, the supernatant obtained when lactic acid-producing bacteria are added to skim milk alone, or in combination with both calcium chloride and acid, and then the resulting casein precipitate is removed by centrifugation or such, can be also used as acid whey.

TABLE 1

| Constituents | Sweet whey | Acid whey |
|---|---|---|
| Total solids | 6.35 | 6.5 |
| Water | 93.7 | 93.5 |
| Fat | 0.5 | 0.04 |
| Total protein | 0.8 | 0.75 |
| Lactose | 4.85 | 4.90 |
| Ash | 0.5 | 0.8 |
| Lactic acid | 0.05 | 0.4 |
| | | (Weight %) |

In sweet whey, about 8% of the total solids is lipids (Table 1). These lipids are said to spoil the flavor of Whey Protein Concentrate (WPC). Further, whey lipids are associated with the efficiency of membrane treatment for ultrafiltration (UF) membranes, reverse osmosis (RO) membranes, and such. Accordingly, the more residual lipid in whey, the slower the flux speed during membrane separation.

In the present invention, whey is centrifuged/purified and adjusted to approximately neutral pH (6.8 to 7.2), then subject to microfiltration. Further, water is added to the retentate, which is then subject to microfiltration, and this process is repeated several (usually three) times. Following this, the retentate is dehydrated by standard methods.

The development of microfiltration for practical application was slow since microfiltration is susceptible to clogging. In mid-1980s, a membrane sterilization system for milk, "Bactocatch", was developed and put into practical use by ALFA-LAVAL Filtration System (now Tetra Pak).

Methods for using MF membranes include those where samples flow parallel to the membrane surface (tangential flow filtration or cross flow filtration), and those where samples are pushed perpendicularly against the membrane surface (dead end filtration). In the dairy industry, cross flow filtration is used to treat dairy products, while dead end filtration is used to eliminate bacteria from the air for a sterile tank.

Bactocatch is a cross flow MF (CFMF) filtration system, where the MF membrane (Membralox, manufactured by SCT in France) is made of alumina ceramics and has micropores 1.4-μm in diameter to stop bacteria but transmit casein micells. The most outstanding characteristic of Bactocatch is that the permeation flux is controlled, allowing operation at a uniform transmembrane pressure (UTP) for the whole module of about 0.04 MPa (0.1 MPa is about 1 atmospheric pressure). This can prevent the membranes from clogging. As a result, for skim milk a permeation flux of 500 L/h can be stabilized at 50° C. for seven hours, while maintaining a bacteria elimination efficiency of 99.9% or more (Olsen, N. et al.: Milchwissenschaft, 44 (8): p. 476, 1989). It has become possible to manufacture Extended Shelf Life (ESL) milk by using milk sterilized using the Bactocatch system as a starting material. Further, this Bactocatch system has been also used to remove spores from cheese materials. In the present invention also, a cross flow filtration system apparatus comprising this Bactocatch system may be used in microfiltration of whey. A dead end filtration system apparatus can also be used in microfiltration of whey. In addition, the shape of MF membranes can differ, such as flat membrane types and hollow fiber types, and the materials can also differ, such as resin membranes and ceramic membranes. Appropriate types of membranes can be used.

The fat in whey cannot be completely removed by centrifugation, and about 0.05% remains. When a WPC powder with a protein content of 80% is produced from this whey, the fat content reaches 5% to 8% (J. L. Maubois: Bulletin of the IDF 320: 37-40, 1997). These lipids are said to cause the functionality and flavor of WPCs to be spoiled (C. V. Morr and E. Y. W. Ha: CRC Crit. Rev. Food Sci. Nutr., 33: p. 431, 1993; J. N. de Wit, G. Klarenbeek and M. Adamse: Neth. Milk Dairy J., 40, p. 41, 1986; M. T. Patel and A. Kilara: J. Dairy Sci., 73: p. 2731, 1990). Further, the whey lipids are associated with the efficiency of membrane treatment using ultrafiltration (UF), reverse osmosis (RO), and such. Thus, the more residual lipid in whey, the slower the flux speed during membrane separation (J. N. de Wit and R. de Boer: Neth. Milk Dairy J., 29, p. 198, 1975). The main constituent of this fat is phospholipid. Most of this fat is removed by treating whey using 0.1-μm MF (P. Dejimek and B. Hallstroem: Shokuhin Maku Gijutsu Kondankai, Fifth Quarterly (Spring) Research Meeting, Abstract, p. 36-45, 1993; A. Nielsen: Danish Dairy & Food Ind. Worldwide, 10: 72-73, 1996).

In general, permeate can be sterilized using an MF membrane with micropores ranging from about 0.2 to 0.45 μm in diameter. Bacteria are almost the same size as fat globules (fat globules range from 0.1 to 17 μm in diameter, and are 3.4 μm on average). The micropores of MF membranes usually range from 0.01 μm to 12 μm in diameter. Although the micropores of MF membranes used in this invention are assumed to practically range from 0.1 to 1.4 μm in diameter, one skilled in the art can confirm the optimization of micropore diameter in routine experiments.

More simply, as in separating fresh cream from raw milk, an aqueous phase can be obtained by centrifuging sweet whey in particular at about 30° C. to 60° C., and further centrifuging the whey cream thus obtained. The aqueous phase thus obtained can be similarly used as the MF retentate.

Further, as a modification of the above-described centrifugation, the acid whey obtained by heat-treating skim milk at 95° C. for 30 minutes, the so-called "proteose-peptone", is treated with a combination of ammonium sulfate precipitation and centrifugation methods, and the fractions thus obtained can be also similarly used as the MF retentate.

The MF retentate of whey, solutions obtained by centrifuging whey, and/or fractions obtained by treating whey with ammonium sulfate precipitation, or the dehydrated products thereof, have activity against rotavirus infection as shown in the following Examples. Further, even after heat treatment these products retain activity against rotavirus infection. MF retentate and the dehydrated products thereof are obtained as by-products of whey protein isolate (WPI), produced by a combination of MF and UF. Solutions obtained by centrifuging whey and the dehydrated products thereof are obtained as butter oil by-products. Phospholipids are concentrated in the MF retentate of whey, the solutions obtained by centrifuging whey, and the dehydrated products thereof produced in this way.

The compositions of this invention can be heat-treated, and can be expected to be effective in preventing or treating diarrhea caused by rotavirus in human infants, calves, colts, and such by mixing with foods (in particular infant formula and feed for calves) in effective doses thereof. Although effective doses of the compositions of this invention are assumed to range from 0.1 to 50 percent by weight of the final products, they should be determined by tests on humans or domestic animals.

Rotavirus proliferates in about the end third of epithelial cells in the villi of the small intestine. After viral infection, these microvilli are dwarfed, causing a pathological change such as disarray or loss of microvilli. As a result, physiological functions are reduced and water absorption is inhibited, leading to diarrhea. The process of rotaviral infection begins with the adhesion to target cells, and includes multiple steps, such as viral penetration and colonization.

The activity against rotavirus infection of the MF retentate of whey, solutions obtained by centrifuging whey, and/or fractions obtained by treating whey with ammonium sulfate precipitation, and the dehydrated products thereof, according to the present invention, is assumed to be due to the inhibition of rotavirus adhesion to target cells by these products. However, further elucidation of the action mechanism is required.

Methods for testing and assessing the effect of food constituents against rotavirus infection are diverse, and there are no absolute tests or assessment systems. Various methods for testing/assessing activity against rotavirus infection have been reported to date. In addition to the methods used in the present invention, these methods comprise, for example, a test/assessment system in which rotavirus and a food constituent are administered to experimental animals (mice), and the onset of diarrhea and the amount of rotavirus bound to gastrointestinal mucosa is assayed and evaluated (Duffy L. C. Pediatr. Res. 35: 690-695 (1994)). The present inventors can examine the activity against rotavirus infection of the compositions in more detail by appropriately using these systems.

The safety of the milk-derived compositions used in this invention has been established over long experience of consumption. Accordingly, the effectiveness and effective dose of a product of the present invention can be confirmed using human tests.

For use as the compositions against rotavirus infection, milk-derived compositions can be used as they are (as liquids or powders), or with other active substances or pharmacologically active substances. The dosage forms comprise, for example, tablets or coated tablets, capsules, solutions, syrups, emulsions, or dispersive powders. Doses thereof vary depending on the age, physical conditions, and such of subjects, ranging from 0.001 to 10 g/kg body weight per day, and preferably 0.01 to 2 g/kg body weight per day.

To prepare the food compositions against rotavirus infection, the milk-derived compositions can be added in their effective doses to infant formula with an undeveloped ability to protect against rotavirus infections, or to food products intended for the elderly, who have a reduced ability to protect against rotavirus infections. The term "infant formula" refers to infant formula intended for newborn to 12-month-old infants, follow-up formula intended for 6- to 9-month-old or older infants and young children (up to 3 years old), preterm formula intended for neonates whose birth weights were less than 2,500 g (low birth weight infants), various formula for treatments used in the treatment of children with morbidities such as milk allergies and lactose intolerance, and such. Further, the compositions can be applied to foods with health claims and food products for the ill. The system of foods with health claims has been established based on domestic and foreign trends, as well as consistency with conventional systems for foods for specified health uses. It includes not only usual foods but also foods in the form of tablets, capsules, and so on. There are two types of foods with health claims: foods for specified health uses (licensed on a case-by-case basis) and foods with nutrient function claims (standard type). Further, the compositions can be added in their effective dose to livestock feeds to prepare compositions against rotavirus infection.

BRIEF DESCRIPTION OF THE DRAWINGS

FIG. 1 depicts the fractionation pattern of active constituents of a composition against rotavirus infection using a gel filtration (Sephacryl S-500) column.

BEST MODE FOR CARRYING OUT THE INVENTION

Hereinbelow, the effects of this invention will be specifically described using Examples, but the invention is not to be construed as being limited thereto.

Example 1

Preparation of Compositions Against Rotavirus Infection from Whey and the Heat-Treated Products Thereof <Materials and Methods>

Unheated raw milk (100 kg) obtained by milking was pasteurized at 72° C. for 15 seconds to prepare Mozzarella cheese according to standard methods. The resulting whey was adjusted to pH6.8 using 6 N NaOH, and centrifuged to remove the cream fraction and minute casein particles. The whey, free of the cream fraction and casein, was treated using a microfiltration unit (Nihon Pall Ltd.; MEMBRALOX, 0.1 μm micropore diameter, inlet pressure 3.0 kg/cm$^2$, and temperature 25° C.) to recover the retentate. Desalted water was added to the retentate thus obtained, which was then treated again with the microfiltration apparatus. This process was repeated three times. The resulting retentate was dried by spray-drying.

The heated product was prepared by dissolving the dry powder obtained above in distilled water to achieve 10 mg/ml, heat-treating the solution at 80° C. for 30 minutes, and then lyophilizing the solution by standard methods.

Example 2

Measurement of the Phospholipid Contents of the Compositions Derived from Normal Cow Milk <Materials and Methods>

The phospholipid contents of the milk-derived compositions produced from milk by using the methods described in Example 1 was measured. Firstly, samples (10 g) were dissolved in 5% NaCl solution (50 ml). Methanol (100 ml) was then added. Next, chloroform (100 ml) was added to the mixture, stirred, and left standing. The chloroform layer was then recovered. This procedure was repeated a further two times. The chloroform layer thus obtained was dried in vacuo, and dissolved in n-hexane (30 ml). N-hexane-saturated 1% aqueous methanol (50 ml) was added to the solution, stirred, and left standing. The methanol layer was then recovered. This procedure was repeated a further two times. The methanol layers thus obtained were dried in vacuo, and dissolved in chloroform:methanol (2:1) to obtain samples for phospholipid measurement. The concentrations of phosphatidylethanolamine (PE), phosphatidylcholine (PC) and sphingomyelin (SM) in the samples thus obtained were measured by HPLC to determine their phospholipid content.

<Results and Discussion>

The results of measuring the phospholipids (percentage by weight) were 0.69% for PE, 1.36% for PC, and 0.85% for SM. Phospholipid content of milk is reported to be 0.04% to 0.05% (Nyu No Kagaku (Science of Milk), Kaminogawa Shuichi, ed., Asakura Shoten, 1996). Therefore, it was confirmed that the phospholipids in milk are condensed in high concentrations in whey MF retentates.

Example 3

Measurement of the Activity of Inhibiting Rotavirus Infection of the Compositions Derived from Mature Bovine Milk, and Heat-Treated Products Thereof <Materials and Methods>

The activity of inhibiting rotavirus infection of the milk-derived compositions produced from milk by the methods described in Example 1, or the heat-treated products thereof, was measured.

The activity of inhibiting infection with human rotavirus MO strain was measured using compositions derived from mature bovine milk, and heat-treated products thereof, as samples, as follows: Human rotavirus MO strain (106 Fluorescent Cell Focus Forming Units (FCFU)/ml), 0.4 ml) and trypsin (20 μg/ml, 0.4 ml) were mixed, and incubated at 37° C. for 30 minutes. Test samples (sterilized by filtration with a 0.45 μm-filter) were diluted to various concentrations with Eagle's medium comprising 10% fetal bovine serum, and 50 μl of each was aliquoted into 0.5-ml Eppendorf tubes. The prepared virus solution (50 μl each) was added to each tube and incubated at 37° C. for one hour.

As a control, Eagle's basal medium (50 μl) comprising 10% fetal bovine serum was used instead of the above-described sample (50 μl). MA-104 cells ($2 \times 10^5$/ml, 100 μl each) derived from rhesus monkey kidney was added to each Eppendorf tube containing this culture solution, and mixed. 20-μl aliquots of each mixture were transferred to corresponding glass slides, and the cells were cultured at 37° C. for 45 hours. The cells were then fixed with acetone. The number of cells infected with human rotavirus was detected by indirect fluorescent antibody analysis using a monoclonal antibody specifically recognizing the VP6 of pigeon rotavirus PO-13 strain as a primary antibody, and fluorescence-labeled goat anti-rabbit IgG antibody as a secondary antibody.

To assess infection inhibitory activity, when the value (inhibition rate) obtained from the equation below is 50% or more, the sample was judged to have infection inhibitory activity, and the lowest sample concentration with infection inhibitory activity was taken as the minimum inhibitory activity.

$$100 \times [1-(\text{number of infected cells when a sample is added})/(\text{number of infected cells in the control})]$$

<Results and Discussion>

The minimum inhibitory activities of the composition derived from mature bovine milk, and the heat-treated product thereof, were 33 and 35 μg/ml (protein concentration determined with bovine serum albumin as standard), respectively. These results prove that the compositions have the activity of inhibiting rotavirus infection, and that this activity is almost unaffected by heat treatment. Further, the compositions of this invention produced from other starting materials and by other methods also gave almost the same results. Therefore, the compositions obtained from cow's milk by separation through a microfiltration membrane were revealed to have the activity of inhibiting rotavirus infection, and their activity of inhibiting rotavirus infection was revealed to be heat-stable.

Infection with rotavirus begins with adhesion target cells, and includes multiple steps, such as viral penetration and colonization. In this study, rotavirus infection was inhibited when the compositions were pre-mixed with rotavirus and then reacted with target cells, suggesting their activity of inhibiting rotavirus infection is manifested by inhibiting rotavirus adhesion to target cells.

Example 4 infant formula consisting of the following formulation was prepared to include 0.5% of the milk-derived composition produced from cow's milk by the method described in Example 1.

TABLE 2

| Constituents | per 100 g product | |
|---|---|---|
| Protein | 11.7 | g |
| Lipid | 25.0 | g |
| Carbohydrate | 58.3 | g |
| (Lactose) | (51.0) | g |
| (Soluble polysaccharide) | (5.0) | g |
| (Fructo-oligosaccharide) | (2.3) | g |
| Ash | 2.2 | g |
| Water | 2.8 | g |
| Energy | 500 | kcal |
| Present composition | 0.5 | g |
| Vitamin A | 1,700 | IU |
| Vitamin B1 | 0.30 | mg |
| Vitamin B2 | 0.60 | mg |
| Vitamin B6 | 0.30 | mg |
| Vitamin B12 | 2.0 | μg |
| Vitamin C | 50 | mg |
| Vitamin D | 370 | IU |
| Vitamin E (as α-tocopherol) | 6.0 | mg |
| Vitamin K | 25 | μg |
| Pantothenic acid | 2.0 | mg |
| Niacin | 6.0 | mg |
| Folic acid | 0.1 | mg |
| β-Carotene | 70 | μg |
| Linoleic acid | 3.5 | g |
| α-Linolenic acid | 0.40 | g |
| Arachidonic acid | 24 | mg |
| Docosahexaenoic Acid | 100 | mg |

TABLE 2-continued

| Constituents | per 100 g product |
| --- | --- |
| Cholesterol | 70 mg |
| Phospholipid | 200 mg |
| Cystine | 180 mg |
| Taurine | 27 mg |
| Nucleic acid-related substances | 14 mg |
| Calcium | 380 mg |
| Magnesium | 40 mg |
| Potassium | 490 mg |
| Sodium | 140 mg |
| Phosphorus | 210 mg |
| Chlorine | 310 mg |
| Iron | 6.0 mg |
| Copper | 320 µg |
| Manganese | 30 µg |
| Selenium | 7.0 µg |
| Carnitine | 13 mg |
| Zinc | 3.0 mg |

Example 5

Preparation of Compositions Inhibiting Rotavirus Infection from Whey and Heat-Treated Products Thereof Unheated raw milk (100 kg) obtained by milking was pasteurized at 72° C. for 15 seconds to prepare Gouda cheese according to standard methods, and the resulting whey was adjusted to pH6.8 with 6 N NaOH. Similarly, Emmenthal cheese was prepared according to standard methods from raw milk (100 kg) treated by HTST method, and the resulting whey was adjusted to pH6.8 with 6 N NaOH. These whey preparations were mixed and centrifuged to remove the cream fraction and minute casein particles. The whey thus obtained was diluted with water to adjust the solid constituent concentration to 1.7%, and treated with a microfiltration apparatus (Exekia ceramic filter, 0.1 µm micropore diameter, inlet pressure 7.5 kg/cm$^2$, temperature 50° C.) to recover the retentate containing 8% solid content. The resulting retentate was further concentrated in vacuo and then dried by spray-drying.

The heated products were prepared by dissolving the powder thus obtained in distilled water to concentrations of 1 mg/ml, 5 mg/ml, and 10 mg/ml, heat-treating the solutions at 141° C. for 5 seconds, and lyophilizing them according to standard methods. The solution dissolved to a concentration of 10 mg/ml was separately treated by heating at 100° C. for 5 minutes and at 80° C. for 30 minutes to prepare other heat-treated products which were then lyophilized by standard methods.

Example 6

Measurement of the Activity of Inhibiting Rotavirus Infection of the Compositions Against Rotavirus Infection Derived from Whey and Heat-Treated Products Thereof <Materials and Methods>

Milk-derived compositions produced from raw milk by the method described in Example 5, or the heat-treated products thereof, were examined for the activity of inhibiting rotavirus infection by the method described in Example 3.

Specifically, human rotavirus MO strain (106 Fluorescent Cell Focus Forming Unit (FCFU)/ml), 0.4 ml) and trypsin (20 µg/ml, 0.4 ml) were mixed and then incubated at 37° C. for 30 minutes. Test samples (50 µl each) (sterilized by filtration using an 0.45-µm filter) were pre-diluted to various concentrations with Eagle's basal medium comprising 10% fetal bovine serum, and aliquoted in to 0.5-ml Eppendorf tubes. The above-prepared virus solutions (50 µl each) were added to each tube and incubated at 37° C. for one hour. As a control, Eagle's medium comprising 10% fetal bovine serum (50 µl) was used instead of the above-described test sample (50 µl). MA-104 cells derived from rhesus monkey kidney ($2\times10^5$/ml, 100 µl) were added to each Eppendorf tube containing the culture solution, and mixed. Each mixture (20-µl aliquot) was transferred onto a corresponding slide glass. After incubating at 37° C. for 45 hours, the cells were fixed with acetone. The number of cells infected with human rotavirus was detected by indirect fluorescent antibody analysis (using a monoclonal antibody specifically recognizing the VP6 of pigeon rotavirus PO-13 strain as a primary antibody, and fluorescence-labeled goat anti-rabbit IgG serum as a secondary antibody). Activity was expressed as a minimum inhibitory concentration, as in Example 3.

<Results and Discussion>

Even when the compositions against rotavirus infection prepared from whey were heat-treated according to the thermal process conditions for manufacturing various foods, their inhibitory activity was hardly reduced, as shown in Table 3. These results suggested this activity is highly likely to be retained in the final products.

TABLE 3

Activity of inhibiting rotavirus infection of the compositions against rotavirus infection from whey and heat-treated products thereof

| Samples | Minimum inhibitory concentrations* (µg/ml) |
| --- | --- |
| Composition against rotavirus infection from whey | 25 |
| Heat-treated product of the composition (0.1% solution heated at 141° C. for 5 seconds) | 27 |
| Heat-treated product of the composition (0.5% solution heated at 141° C. for 5 seconds) | 34 |
| Heat-treated product of the composition (1% solution heated at 141° C. for 5 seconds) | 39 |
| Heat-treated product of the composition (1% solution heated at 100° C. for 5 minutes) | 13 |
| Heat-treated product of the composition (1% solution heated at 80° C. for 30 minutes) | 20 |

*Minimum inhibitory concentrations are expressed as protein concentrations determined with bovine serum albumin as standard.

Example 7

Compositions Against Rotavirus Infection Prepared from Whey by Using Microfiltration Membranes having Micropores of Various Diameters Unheated raw milk (100 kg) obtained by milking was treated by centrifugation (8,000×g, 15 minutes, 4° C.) to separate cream and obtain skim milk. This skim milk was warmed (20° C. to 25° C.) and adjusted to pH4.6 by adding 0.5 N HCl. The skim milk was kept in this state for 15 to 30 minutes and centrifuged (3,000×g, 15 minutes, 4° C.) to separate casein and obtain acid whey. This acid whey was adjusted to pH6.0 by adding 0.5 N NaOH, and treated by microfiltration using microfiltration membranes (cellulose mixed ester type, AdvantecToyo Kaisha, Ltd) of various micropore diameters (0.1, 0.2, 0.3, 0.45, 0.65, 0.8, and 1.0 μm). The treatment conditions at this time were: inlet pressure 3.0 kg/cm$^2$; temperature 20° C. to 25° C. Firstly, acid whey was concentrated 5-fold using a microfiltration membrane. Then, while adding water to the concentrated solution, it was subjected to diafiltration until the Brix value of the liquid transmitted from the microfiltration membrane was less than 2%. Finally, microfiltration retentate was lyophilized by standard methods, and further treated by γ-ray irradiation to obtain test samples.

Example 8

Measurement of the Activity of Inhibiting Rotavirus Infection of the Compositions Against Rotavirus Infection Prepared from Whey Using Microfiltration Membranes with Micropores of Various Diameters <Materials and Methods>

The activity of inhibiting rotavirus infection of the compositions against rotavirus infection produced from raw milk by the method described in Example 7 was measured by the method described in Example 6.

<Results and Discussion>

The results of measuring the anti-rotavirus activity of each sample are shown in Table 4. The minimum inhibitory concentrations of the test samples are expressed as protein concentrations determined with bovine serum albumin as standard.

The results show that when the micropore diameter of the MF membrane was 0.8 μm or more, the anti-rotavirus activity of MF retentate was remarkably reduced. Therefore, when preparing compositions against rotavirus infection from whey, it seemed preferable to use a microfiltration membrane with a micropore diameter of 0.65 μm or less.

TABLE 4

The activity of inhibiting rotavirus infection of the compositions against rotavirus infection prepared from whey using microfiltration membranes with micropores of various diameters

| Samples<br>Products retained through: | Minimum inhibitory concentration*<br>(μg/ml) |
|---|---|
| 0.1 μm micropore diameter | 25 |
| 0.2 μm micropore diameter | 81 |
| 0.3 μm micropore diameter | 36 |
| 0.45 μm micropore diameter | 52 |
| 0.65 μm micropore diameter | 61 |
| 0.8 μm micropore diameter | >81 |
| 1.0 μm micropore diameter | >101 |

*Minimum inhibitory concentrations were expressed as protein concentrations determined with bovine serum albumin as standard.

Example 9

Compositions Against Rotavirus Infection Prepared from Whey by Centrifugation

Unheated raw milk (100 kg) obtained by milking was pasteurized at 63° C. for 30 minutes to prepare Camembert cheese according to standard methods. The resulting whey was separated (pH6.0), warmed, and centrifuged (3,000×g, 20 minutes, 40° C.) to obtain whey cream. Further, this whey cream was again warmed to 50° C. and centrifuged (3,000×g, 20 minutes, 50° C.). The aqueous phase thus obtained (hereinafter abbreviated to whey cream serum) was lyophilized by standard methods to obtain test samples.

Example 10

Measurement of the Activity of Inhibiting Rotavirus Infection of the Compositions Against Rotavirus Infection Prepared from Whey by Centrifugation <Materials and Methods>

The activity of inhibiting rotavirus infection of compositions against rotavirus infection produced from raw milk by the method described in Example 9 was measured by the method described in Example 6. Further, bovine lactoferrin (DMV) was used as a control sample for comparison.

<Results and Discussion>

The results of measuring the anti-rotavirus activity of each sample are shown in Table 5. The minimum inhibitory concentrations of test samples act expressed as protein concentrations determined with bovine serum albumin as standard.

Whey cream serum showed a strong anti-rotavirus activity, exceeding that of bovine lactoferrin.

Accordingly, it was revealed that the compositions against rotavirus infection can be prepared from whey merely by centrifugation.

TABLE 5

The activity of inhibiting rotavirus infection of the compositions against rotavirus infection prepared from whey by centrifugation

| Samples | Minimum inhibitory concentrations*<br>(μg/ml) |
|---|---|
| Whey cream serum | 65 |
| Bovine lactoferrin | 1787 |

*Minimum inhibitory concentrations are expressed as protein concentrations determined with bovine serum albumin as standard.

Example 11

Compositions Against Rotavirus Infection Prepared by Ammonium Sulfate Precipitation and Centrifugation of Whey Obtained from Skim Milk Heat-Treated at 95° C. for 30 Minutes Unheated raw milk (10 kg) obtained by milking was centrifuged (8,000×g, 15 minutes, 4° C.) to separate cream and obtain skim milk. This skim milk was heat-treated (95° C., 30 minutes) and adjusted to pH4.6 by adding 0.5 N HCl. The skim milk was kept in this state for 15 to 30 minutes, and centrifuged (5,000×g, 30 minutes, 4° C.) to separate casein and obtain acid whey. Ammonium sulfate was added to the acid whey until 35% saturation. This solution was centrifuged (7,000×g, 30 minutes, 4° C.) to remove the precipitate. Ammonium sulfate was again added to the precipitate-free solution, this time until 55% saturation. This solution was again centrifuged (7,000×g, 30 minutes, 4° C.) to remove the precipitate. Ammonium sulfate was further added to the solution thus obtained, to reach 90% saturation. Finally, this solution was centrifuged (7,000×g, 30 minutes, 4° C.) to recover the precipitate. The precipitate obtained from the solution at 90% saturation was dissolved in distilled water, then dialyzed with distilled water, and lyophilized by standard methods to obtain test samples.

Example 12

Measurement of the Activity of Inhibiting Rotavirus Infection of the Compositions Against Rotavirus Infection Prepared by Ammonium Sulfate Precipitation and Centrifugation of Whey Obtained from Skim Milk Heat-Treated at 95° C. for 30 Minutes <Materials and Methods>

The activity of inhibiting rotavirus infection of the compositions against rotavirus infection produced from raw milk by the method described in Example 11 was measured by the method described in Example 6.

<Results and Discussion>

The precipitate obtained at 90% saturation showed a minimum inhibitory concentration of 50 μg/ml (protein concentration determined with bovine serum albumin as standard).

Thus, it was revealed that the ammonium sulfate-precipitated fraction of whey obtained from skim milk heat-treated at 95° C. for 30 minutes, so-called proteose-peptone, has anti-rotavirus activity.

Example 13

Fractionation of Active Constituents of the Compositions Against Rotavirus Infection Using a Gel Filtration Column and Ammonium Sulfate The active constituents of the milk-derived compositions produced from raw milk by the method described in Example 5 were further fractionated.

The powder obtained by spray-drying the retentate in Example 5 was dissolved in distilled water to make a 5% solution, and then heat-treated at 95° C. for 30 minutes. An aliquot of this solution was dialyzed overnight against Tris-HCl buffer, as described below, to obtain a sample for gel filtration.

The solvent of Sephacryl S-500 HR (about 480 ml) was replaced with Milli-Q water (extra pure water) by decantation, repeated several times. The gel was stirred until homogeneous, and gently poured into a column (2.6×60 cm) equipped with a reservoir. The reservoir was then filled with Milli-Q water and covered to exclude air. The column was connected to an AKTA explorer 10 C (Amersham Pharmacia Biotech). Milli-Q water was poured into the column to sediment the gel to a sufficient degree, and then the reservoir was detached to attach the adapter. This column was equilibrated with 0.05 M Tris-HCl buffer, pH8.0 (0.15 M NaCl, 1 mM $Na_2EDTA$, 0.02% $NaN_3$). The above-described sample (11 ml) was applied to the column, and eluted at a flow rate of 1.3 ml/minute. During this process, changes in absorbance of the eluate at 280 nm were monitored to recover the fraction C1 which mostly passed through the column. This fraction C1 was dialyzed against distilled water overnight, and then a portion thereof was lyophilized by standard methods to be used as a test sample. The residual portion was further fractionated using ammonium sulfate as in Example 11. Specifically, ammonium sulfate was added to this C1 fraction solution until 35% saturation. This solution was centrifuged (7,000×g, 30 minutes, 4° C.) to remove precipitates. Ammonium sulfate was again added to the precipitate-free solution, this time to reach 55% saturation. This solution was centrifuged (7,000×g, 30 minutes, 4° C.) to again remove precipitates. Ammonium sulfate was further added to the solution thus obtained until 90% saturation. Finally, this solution was centrifuged (7,000×g, 30 minutes, 4° C.) to recover the precipitate. The precipitate obtained from the solution at 90% saturation was dissolved in distilled water, then dialyzed against distilled water, and lyophilized by standard methods to obtain a test sample.

Example 14

Measurement of the Activity of Inhibiting Rotavirus Infection of the Constituents Obtained by Fractionating Compositions Against Rotavirus Infection Using Gel Filtration (Sephacryl S-500) Column and Ammonium Sulfate <Materials and Methods>

The activity of inhibiting rotavirus infection of the constituents produced from raw milk by the method described in Example 13 was measured by the method described in Example 6.

<Results and Discussion>

The results of measuring the anti-rotavirus activity of each sample are shown in Table 6. The minimum inhibitory concentrations of the test samples are expressed as protein concentrations determined with bovine serum albumin as standard.

It was revealed that the active constituent is condensed by salting out with ammonium sulfate after treatment with a gel filtration column.

TABLE 6

Activity of inhibiting rotavirus infection of the constituent obtained by fractionation using gel filtration (Sephacryl S-500) column and salting out with ammonium sulfate

| Samples | Minimum inhibitory concentrations* (μg/ml) |
|---|---|
| C1 | 52 |
| Fraction salted out at 90% saturation with ammonium sulfate | 11 |

*Minimum inhibitory concentrations are expressed as protein concentrations determined with bovine serum albumin as standard.

Example 15

Fractionation of the Active Constituents of the Compositions Against Rotavirus Infection by Centrifugation and Ultrafiltration The active constituents of the milk-derived compositions produced from raw milk by the method described in Example 5 was further fractionated.

The powder obtained by spray-drying the retentate in Example 5 was dissolved in distilled water to make a 10% solution, and then adjusted to pH4.6 by adding 0.5 N HCl. The solution was kept in this state for 15 to 30 minutes, and centrifuged (6,000×g, 20 minutes, 4° C.) to separate into precipitant and supernatant fractions. The precipitant fraction was dispersed in distilled water again, and then lyophilized by standard methods to obtain test sample A. The supernatant fraction was subjected to ultrafiltration using an ultrafiltration membrane with a fractionation molecular weight of 10,000 (Nihon Millipore). The treatment temperature was 20 to 25° C. First, the supernatant fraction was concentrated to ¼ volume using the ultrafiltration membrane. Next, the concentrated solution was diluted 4-fold by adding water, and then subjected to diafiltration to again reduce the volume to ¼. The finally obtained retentate of the ultrafiltration membrane was lyophilized by standard methods to obtain test sample B.

Example 16

Measurement of the Activity of Inhibiting Rotavirus Infection of the Constituents Obtained by Fractionating Compositions Against Rotavirus Infection by Centrifugation and Ultrafiltration <Materials and Methods>

The activity of inhibiting rotavirus infection of the constituents produced from raw milk by the method described in Example 15 was measured by the method described in Example 6. Further a non-fractionated sample was used as a control sample, for comparison.

<Results and Discussion>

The results of measuring the anti-rotavirus activity of each sample are shown in Table 7. The minimum inhibitory concentrations of test samples are expressed as protein concentrations determined with bovine serum albumin as standard.

It was revealed that the active constituent is concentrated by centrifugation and ultrafiltration.

TABLE 7

Activity of inhibiting rotavirus infection of constituents obtained by fractionation through centrifugation and ultrafiltration

| Samples | Minimum inhibitory concentrations* (μg/ml) |
| --- | --- |
| Unfractionated | 49 |
| A | 19 |
| B | 16 |

*Minimum inhibitory concentrations are expressed as protein concentrations determined with bovine serum albumin as standard.

INDUSTRIAL APPLICABILITY

The present invention provides novel compositions with the activity of protecting against rotavirus infection. An effective dose of the compositions can be combined in infant formula.

The invention claimed is:

1. A method of preventing rotavirus infection, comprising administering a composition that comprises a microfiltration retentate of whey, or a dehydrated product thereof, wherein the antiviral activity of said composition is retained after heat treatment, wherein said heat treatment is conducted at 80° C.×30 minutes, 100° C.×5 minutes, or 141° C.×5 seconds.

2. The method of claim 1, wherein the microfiltration is carried out by using a microfiltration membrane having a micropore diameter ranging from 0.004 to 1.4 μm.

3. The method of claim 1, wherein the composition is a food.

4. The method of claim 3, wherein the food is selected from the group consisting of infant formula, a food product for the elderly, a food with health claims, and a food product for the ill.

5. The method of claim 1, wherein the composition is a livestock feed.

* * * * *

UNITED STATES PATENT AND TRADEMARK OFFICE
CERTIFICATE OF CORRECTION

PATENT NO. : 8,211,476 B2
APPLICATION NO. : 10/548906
DATED : July 3, 2012
INVENTOR(S) : Yoshihiro Kanamaru et al.

It is certified that error appears in the above-identified patent and that said Letters Patent is hereby corrected as shown below:

Column 1,
Line 49, "ic-casein" should read --κ-casein--

Column 7,
Lines 48-49, "strain (106 Fluorescent Cell Focus Forming Units (FCFU)/ml)" should read --strain ($10^6$ Fluorescent Cell Focus Forming Units (FCFU)/ml)--

Column 9,
Lines 64-65, "strain (106 Fluorescent Cell Focus Forming Unit (FCFU)/ml)" should read --strain ($10^6$ Fluorescent Cell Focus Forming Unit (FCFU)/ml)--

Signed and Sealed this
Ninth Day of October, 2012

David J. Kappos
*Director of the United States Patent and Trademark Office*